US00PP33811P3

(12) United States Plant Patent
Post

(10) Patent No.: US PP33,811 P3
(45) Date of Patent: Jan. 4, 2022

(54) ***CHRYSANTHEMUM* PLANT NAMED 'DLFSHAD3'**

(50) Latin Name: ***Chrysanthemum* X *morifolium***
Varietal Denomination: DLFSHAD3

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/170,611

(22) Filed: Feb. 8, 2021

(65) Prior Publication Data

US 2021/0251123 P1 Aug. 12, 2021

Related U.S. Application Data

(60) Provisional application No. 62/995,750, filed on Feb. 12, 2020.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05)

(58) Field of Classification Search
USPC ..... Plt./286, 297
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFSHAD3', characterized by its upright plant habit; uniform growth habit; dark green-colored leaves; uniform and freely flowering habit; strong upright flowering stems; daisy-type inflorescences with light purple-colored ray florets and bright yellow green-colored disc florets; resistance to Fusarium and White Rust; relatively tolerant to high and low temperatures; and good postproduction longevity.

2 Drawing Sheets

Figure 1:
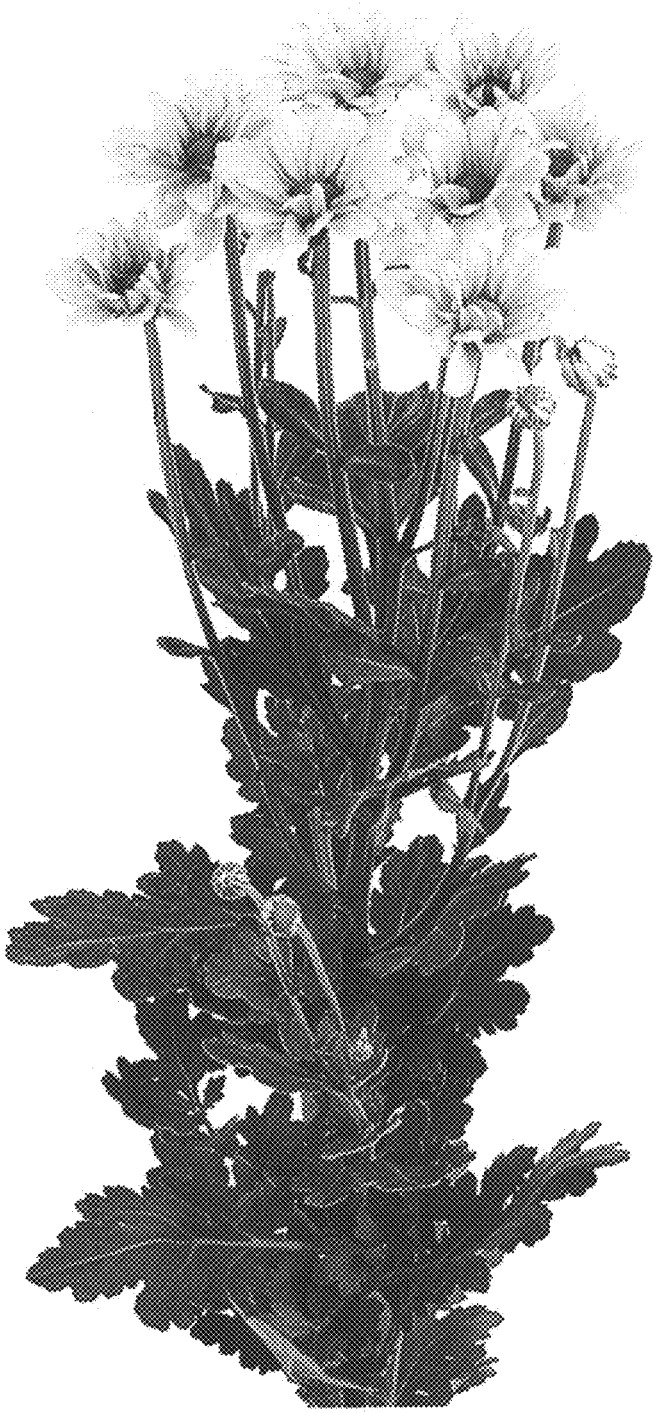

Botanical designation: *Chrysanthemum* X *morifolium*.
Cultivar denomination: 'DLFSHAD3'.

CROSS-REFERENCED TO CLOSELY-RELATED APPLICATIONS

Title: Varieties of *Chrysanthemum* Plants
Inventor/Applicant: Arie Gerard Post
Filed: Feb. 12, 2020
Ser. No.: 62/995,750
Inventor/Applicant hereby claims the benefit of this provisional U.S. Patent Application.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B.V. of Maasdijk, The Netherlands on Mar. 19, 2020, application number 2020/0784.

A Japanese Plant Breeder's Rights application for the instant plant was filed by the Assignee, Deliflor Royalties B.V. of Maasdijk, The Netherlands on Oct. 14, 2020, application number 35003.

Foreign priority is not claimed to either of these applications.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFSHAD3'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in February, 2015 of a proprietary selection of *Chrysanthemum* x *morifolium* identified as code number db 34294, not patented, as the female, or seed, parent with a proprietary selection of *Chrysanthemum* x *morifolium* identified as code number db 10460, not patented, as the male, or pollen, parent. The new *Chrysanthemum* plant was discovered and selected as a single flowering plant from within the progeny of the stated cross-pollination in a controlled greenhouse environment in Maasdijk, The Netherlands in March, 2016.

Asexual reproduction of the new *Chrysanthemum* plant by vegetative terminal cuttings since March, 2016 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFSHAD3'. These characteristics in combination distinguish 'DLFSHAD3' as a new and distinct *Chrysanthemum* plant:

1. Upright plant habit; uniform growth habit.
2. Dark green-colored leaves.
3. Uniform and freely flowering habit.
4. Strong upright flowering stems.
5. Daisy-type inflorescences with light purple-colored ray florets and bright yellow green-colored disc florets.
6. Resistant to Fusarium and White Rust.
7. Relatively tolerant to high and low temperatures.
8. Good postproduction longevity.

Plants of the new *Chrysanthemum* differ primarily from plants of the female parent selection in ray floret color as ray florets of plants of the new *Chrysanthemum* are light purple in color whereas ray florets of plants of the female parent selection are light purplish pink in color. In addition, ray florets of plants of the new *Chrysanthemum* reflex with development whereas ray florets of plants of the female parent selection do not reflex with development.

Plants of the new *Chrysanthemum* differ primarily from plants of the male parent selection in ray floret color as ray florets of plants of the new *Chrysanthemum* are light purple red in color whereas ray florets of plants of the male parent selection are white in color.

Plants of the new *Chrysanthemum* can be compared to plants of *Chrysanthemum* X *morifolium* 'Chelo', not patented. In side-by-side comparisons, plants of the new *Chrysanthemum* differ primarily from plants of 'Chelo' in ray floret color as plants of the new *Chrysanthemum* have light purple-colored ray florets whereas plants of plants of 'Chelo' have darker purple-colored ray florets. In addition, ray florets of plants of the new *Chrysanthemum* are more convex than ray florets of plants of 'Chelo'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFSHAD3' grown as a spray-type cut flower.

Figure 2:
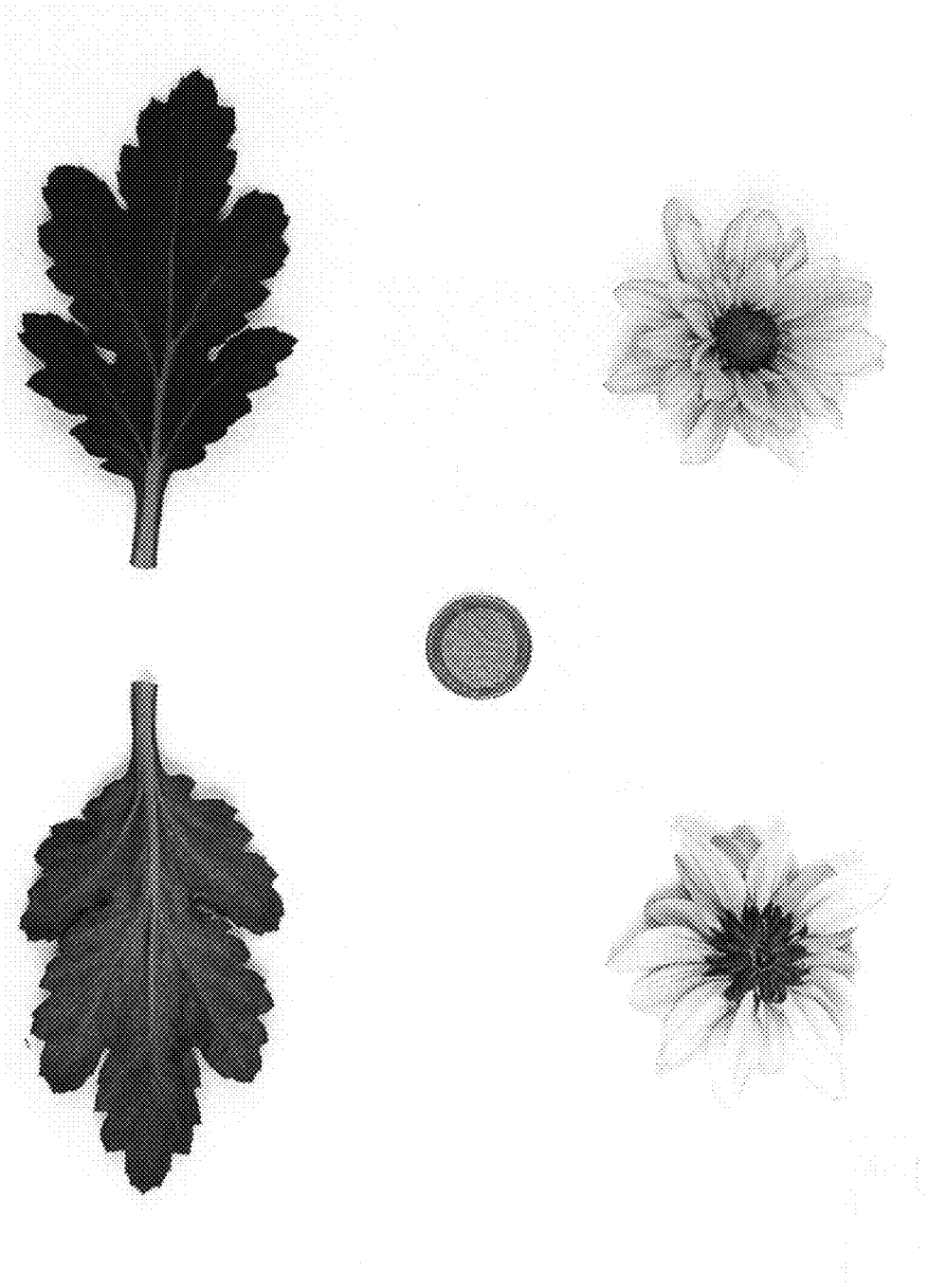

The photograph on the second sheet (FIG. 2) is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFSHAD3'.

Parentage:

*Female, or seed, parent*.—Proprietary selection of *Chrysanthemum* x *morifolium* identified as code number db 34294, not patented.

*Male, or pollen, parent*.—Proprietary selection of *Chrysanthemum* x *morifolium* identified as code number db 10460, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 80.8 cm.

*Plant height, soil level to top of inflorescence plane*.—About 89.4 cm.

*Plant (spray) diameter*.—About 20.7 cm.

*Flowering stem length*.—About 78.5 cm.

*Flowering stem diameter*.—About 7.5 mm.

*Flowering stem internode length*.—About 1.9 cm.

*Flowering stem strength*.—Strong.

*Flowering stem aspect*.—Erect.

*Flowering stem texture and luster*.—Densely pubescent; slightly glossy.

*Flowering stem color, developing*.—Close to 144B.

*Flowering stem color, developed*.—Close to 146B; surfaces directly exposed to sunlight, close to 146B strongly tinged with close to 197A.

*Leaf description*.—Arrangement: Alternate; simple. Length: About 10.8 cm. Width: About 6.2 cm. Shape, in outline: Elliptic to obovate. Apex: Abruptly acute, minute. Base: Attenuate. Margin: Palmately lobed, coarsely serrate to dentate; sinuses convergent and medium to deep in depth. Texture and luster, upper surface: Sparsely to moderately pubescent, not rugose; slightly velvety; slightly glossy. Texture and luster, lower surface: Densely pubescent, prominent venation; slightly velvety; very slightly glossy. Venation pattern: Pinnate, reticulate. Color: Developing leaves, upper surface: Close to 137A to 137B. Developing leaves, lower surface: Close to 138B. Fully developed leaves, upper surface: Close to between NN137A and 147A; venation, close to 146B. Fully developed leaves, lower surface: Close to 147B; venation, close to 146B to 146C. Petioles: Length: About 1.7 cm. Diameter: About 3 mm by 4 mm. Strength: Moderately strong. Texture and luster, upper and lower surfaces: Moderately pubescent; slightly glossy. Color, upper surface: Close to between 146B and 147C; edges, close to NN137A. Color, lower surface: Close to 146B to 146C; edges, close to 147A to 147B. Stipules: Quantity and appearance: Two leafy stipules, opposite, at the petiole attachment to the stem. Length: About 1.1 cm. Width: About 1 cm. Shape, in outline: Obovate to reniform with one to three shallow to deep incisions. Texture and luster, upper surface: Sparsely to moderately pubescent; slightly glossy. Texture and luster, lower surface: Densely pubescent; very slightly glossy. Color: Upper surface: Close to between NN137A and 147A; venation, close to 146B. Lower surface: Close to 147B; venation, close to 146B to 146C.

Inflorescence description:

*Appearance*.—Spray-type inflorescence form with elliptic to obovate-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 22 inflorescences develop per flowering stem.

*Inflorescence size*.—Diameter, grown as a spray-type: About 6.6 cm. Depth (height), grown as a spray-type: About 2.9 cm. Disc diameter: About 1.6 cm.

*Receptacles*.—Height: About 3.5 mm. Diameter: About 7 mm. Shape: Flattened globular. Color: Close to 145C.

*Inflorescence buds*.—Height: About 1.2 cm. Diameter: About 1 cm. Shape: Ovoid. Texture and luster: Distally, smooth and glabrous; proximally, moderately to densely pubescent; slightly glossy. Color: Close to 137A to 137B; immature ray florets, close to 69D.

*Ray florets*.—Quantity and arrangement: About 28 arranged in about two whorls. Length: About 3.05 cm, varying between 2.9 cm and 3.2 cm. Width: About 1.05 cm, varying between 1 cm and 1.1 cm. Shape: Elliptic to obovate; mostly flat, slightly carinate. Apex: Obtuse to shallowly retuse. Base: Attenuate. Margin: Entire; not undulate. Aspect: About 10° to 60° from vertical. Texture and luster, upper surface: Smooth, glabrous; velvety; very slightly glossy. Texture and luster, lower surface: Smooth, glabrous; very slightly velvety; moderately glossy. Color: When opening, upper surface: Close to between 75C and 76B. When opening, lower surface: Close to 76D. Fully opened, upper surface: Close to 75D; towards the base, close to 75B; venation, similar to lamina color; with development, color becoming closer to 69D to lighter than 69D and towards the base, close to 75C. Fully opened, lower surface: Close to 69C; venation, similar to lamina color; color becoming closer to 69D with development.

*Disc florets*.—Quantity and arrangement: About 200 massed at the center of the receptacle. Length: About 7 mm. Diameter: About 1 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Close to 145C; towards the apex, close to 154B. Color, fully opened, inner and outer surfaces: Close to 145C; towards the apex, close to 154B.

*Involucral bracts*.—Quantity and arrangement: About 32 arranged in about three whorls. Length: About 9 mm. Width: About 3.5 mm. Shape: Ovate to narrowly ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Slightly darker than 143A; lateral margins, translucent and close to 157D and apical margins, close to N199A. Color, lower surface: Close to 137A; lateral margins, translucent and close to 157D and apical margins, close to N199A.

*Peduncles*.—Length, terminal peduncle: About 7.4 cm. Diameter, terminal peduncle: About 3 mm. Length, third peduncle: About 9.2 cm. Diameter, third peduncle: About 3 mm. Strength: Strong. Aspect, terminal peduncle: Upright. Aspect, third peduncle: About 40° from the flowering stem axis. Texture and luster: Densely pubescent; slightly glossy. Color: Close to 138A to 138B.

*Reproductive organs*.—Androecium: Present on disc florets only. Quantity: About five per floret. Filament length: About 3 mm. Filament color: Close to 145C. Anther size: About 0.5 mm by 2 mm. Anther shape: Narrowly oblong. Anther color: Close to 153B. Pollen amount: Scarce. Pollen color: Close to 14A. Gynoecium: Present on both ray and disc florets. Quantity: One per floret. Pistil length: About 5.5 mm. Style length: About 4 mm. Style color: Close to 154C. Stigma diameter: About 1 mm. Stigma shape: Cleft, decurrent. Stigma color: Close to 153D. Ovary color: Close to 157C.

*Seeds and fruits*.—To date, seed and fruit production have not been observed on plants of the new *Chrysanthemum*.

Pathogen & pest resistance & tolerance: Plants of the new *Chrysanthemum* have been observed to be resistant to Fusarium Wilt (*Fusarium oxysporum* spp. *chrysanthemi* (strain FoNL1)) and White Rust (*Puccinia horiana* P. Henn. (strains PhNL1 and PhBE6)) and to be tolerant to Western Flower Thrips (*Frankliniella occidentalis*). To date, plants of the new *Chrysanthemum* have not been observed to be resistant or tolerant to other pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFSHAD3' as illustrated and described.

* * * * *